United States Patent [19]

Yasuki et al.

[11] Patent Number: 4,649,895
[45] Date of Patent: Mar. 17, 1987

[54] EXOTHERMIC COMPOSITION

[75] Inventors: Ryuichi Yasuki, Osaka; Toshitsugu Sahara, Izumi, both of Japan

[73] Assignee: Kiribai Chemical Industry Co., Osaka, Japan

[21] Appl. No.: 846,418

[22] Filed: Mar. 31, 1986

[30] Foreign Application Priority Data

Jul. 18, 1985 [JP] Japan .................. 60-159281

[51] Int. Cl.⁴ ................................. F24J 1/00
[52] U.S. Cl. ..................... 126/263; 44/3 R; 252/67
[58] Field of Search ............... 126/263, 204; 44/3 R, 44/3 B, 3 A; 252/70, 67

[56] References Cited

U.S. PATENT DOCUMENTS 3,976,049  8/1976  Yamashita et al. .............. 126/263

Primary Examiner—Randall L. Green
Attorney, Agent, or Firm—Armstrong, Nikaido, Marmelstein & Kubovcik

[57] ABSTRACT

Exothermic compositions which contain iron powders treated with sulfur-containing compounds as agents to be oxydized and mugwort leaf dry powders as a part of water holding agents. According to the compositions there are provided body warmers having an excellent initial heat generation, water holding capacity, and handling property.

8 Claims, No Drawings

EXOTHERMIC COMPOSITION

BACKGROUND OF THE INVENTION

The present invention relates to exothermic compositions comprising iron metals, neutral metal salts, water, and water holding agents, which generate heat by air oxidation of the iron metals, and more particularly to exothermic compositions which are excellent in heat elevation at the initial stage and are improved in handling.

Recently, exothermic compositions utilizing heat generated by air oxidation of iron metals have been widely sold as body warmers because they can be readily and safely handled without requiring fire. Known body warmers are produced by mixing iron metals, neutral metal salts, water, water holding agents, and the like, and packing the mixture in a bag, and then sealing the bag.

As the iron metals, there are employed granular iron and powdered iron having a large reaction area since these facilitate the oxidation reaction. Further, reduced iron powders prepared by a reduction method are popularly used.

Nevertheless, because the air oxidation of iron is essentially not vigorous, it takes about 3 or 4 hours to reach an equilibrium temperature (generaly 50° to 60° C.). Particularly in cold regions heat generation is inferior at the initial stage, and sometimes heat generation cannot be obtained.

As mentioned above, the exothermic compositions utilize heat generation by air oxidation of iron powders. In order to proceed with the reaction, water and chlorine ion or sulfate ion can be used. Amount of water is preferably such an amount that the sufaces of the iron powders are partially covered with water. When the amount of water is too small, water is consumed in a short time due to evaporation by the heat elevation, which results in termination of the main reaction. When the amount of water is too large, the surfaces of the iron powders are wholly covered with water reducing air-permeability, which prevents the iron from air-oxidation. For holding a suitable amount of water while maintaining a good air-permeability, there have been employed water holding agents such as powders of coconut husk, charcoal, wood, silica gel, vermiculite, pearlite, polyurethane foam, asbestos, water absorbing resin, and the like.

Since the water holding agents are, as mentioned above, used for holding water which is an essential component for the air-oxidation of iron, it is desired that the agents be lighter and cheaper and that the amount of the agents is as small as possible provided that the above condition can be obtained.

An object of the present invention is to provide exothermic compositions which are improved in heat elevation at the initial stage.

Another object of the present invention is to provide exothermic compositions which have an excellent water holding capacity and are improved in handling.

SUMMARY OF THE INVENTION

The present invention relates to exothermic compositions comprising iron metals, nuetral metal salts, water and water holding agents, housing improvements in that iron powders treated with sulfur-containing compounds are used as the iron metals and that dry powders of mugwort leaves from which veins are removed are used as a part of the water holding agents.

According to the present invention, there can be provided exothermic compositions which can quickly generate heat at the initial stage and which are excellent in water holding capacity and in handling. The time required for reaching an equilibrium temperature can be shortened to ½ to 1/10 of the conventionally required time in the case of using untreated iron powders.

DETAILED DESCRIPTION

In the present invention, there can be used various sulfur-containing compounds for treating the iron powders. From viewpoints of price, commercial availability and handling safety, preferred examples of the sulfur-containing compounds are, for instance, simple sulfur; inorganic sulfur-containing compounds such as sodium salts and ammonium salts of sufuric acid, thiosufuric acid, sulfurous acid or sulfamic acid, and sulfides such as ammonium sulfide, ammonium hydrosulfide or ammonium polysulfide; organic sulfur-containing compounds such as thioglycollic acid, thiourea and sodium diethyldithiocarbamic acid; and mixtures thereof. Among these suflur- and nitrogen-containing compounds such as ammonium sulfate and ammonium thiosulfate are most preferably employed in view of safety.

The treated iron powders in the present invention can be prepared by thermally treating iron powders with the sulfur-containing compounds. When using solid sulfur-containing compounds, the thermal treatment can be carried out in a number of ways thermal treatment may be performed by uniformly mixing the iron powder with the sulfur-containing compound powder, and then heating the mixture. It may also be performed by preparing a solution of the sulfur-containing compound, applying the solution to the iron powder or dipping the iron powder into the solution, drying the solution to uniformly coat the surface of the iron, and then heating. Also, the treatment may be by preparing a solution of the sulfur-containing compound, adding the iron powder to the solution, and then heating the iron powder in the solution. When using liquid sulfur-containing compounds at normal temperature, the thermal treatment can be carried out by applying the liquid compound or a solution thereof to the iron powder and heating.

The amount of the sulfur-containing compounds to be used varies with the kind of compounds, particle sizes or the kind of iron powders, treating temperatures, treating methods and the like, and is generally a small amount. For example, 0.01 to 90 g of ammonium sulfate is used on the basis of 200 g of the iron powder. In the case of ammonium thiosulfate and ammonium sulfamate, amounts to be used are 0.005 to 50 g and 0.07 to 80 g, respectively.

The treating temperature varies with the kind of sulfur-containing compounds, treating methods and treating time, and is generally 10 minutes to 3 hours at 100° to 450° C.

It seems that the surface of the iron powder may be partially converted to iron sulfides by the thermal treatment with the sulfur-containing compounds, but it has not yet been clearly studied. As mentioned hereinafter, however, the effects of the invention cannot be obtained when using iron sulfides.

As the iron powders to be treated, there can be employed reduced iron powders, iron powders prepared by an atomization method. When the particle size of the iron powder is reduced, the time for the initial heat elevation becomes shorter. The preferable range of the particle size is 32 meshes pass, most preferably 80 to 145 meshes. Iron powders having a smaller particle size are inferior in handling.

Another characteristic feature of the present invention is the use of the dry powder of mugwort leaves from which veins are removed (hereinafter referred to as "mugwort leaf powder") as a part of the water holding agent. The veins of mugwort leaf are used as a material for preparing moxa, and the mugwort leaf powder used in the present invention can be obtained as a waste from the preparation of moxa. Accordingly the mugwort leaf powder has been discarded or used as a filler for cattle feed. Therefore, it is very inexpensive.

The mugwort leaf powder can be prepared by solar drying. Since the particle size of the mugwort leaf powder used as cattle feed is too large to uniformly disperse the powder to the other components the powder should be further micronized. Preferred mugwort leaf powder contains a powder of 100 meshes pass in an amount of not less than 30% (% by weight, hereinafter the same), more preferably 40 to 80%.

Exothermic compositions generally contain 40 to 80 parts (parts by weight, hereinafter the same) of water on the basis of 100 parts of the iron powder. Accordingly the water holding agents are added in an amount which is sufficient to hold such an amount of water. In order to hold 100 parts of water, about 80 parts of the conventional water holding agent is required. When mugwort leaf powder is used it is required in a smaller amount, only about 60 parts, because the mugwort leaf powder has an excellent water holding capacity.

The mugwort leaf powder is used in a mixture with other conventional water holding agents such as water absorbing resin powders, vermiculite powders, wood powders, pearlite powders, polyurethane foam powders, silica gel powders, coconut husk charcoal powders and asbestos powders. The other water holding agents may be used in an amount of 45 to 95% of the total amount of the water holding agents.

The exothermic compositions of the present invention contain water and neutral metal salts other than the above components, and if necessary, oxidation catalysts. Examples of the neutral metal salts are, for instance, sodium chloride, potassium chloride, calcium chloride, sodium sulfate, and the like. In view of price and the like, sodium chloride is preferably employed. As the oxidation catalyst, active carbon powders are preferably employed. The active carbon powder may be used in mixture with the coconut husk charcoal powder.

When using untreated iron powders, a gas is produced. For preventing the gas generation, it is known to blend, as gas generation inhibitors, inorganic or organic alkali compounds or alkali weak acid salts such as sodium hydroxide, potassium hydroxide, sodium hydrogen carbonate, sodium carbonate, calcium hydroxide, calcium carbonate, and sodium propionate. When adding such gas generation inhibitors, however, heat generation is reduced. According to the present invention, since the iron powder treated with the sulfur-containing compound can reduce gas generation, the gas generation inhibitors may not be added. It should be noted, however, that the present invention is not restricted within the scope where the inhibitors are not used.

According to the present invention, there may be employed usual untreated iron powders together with the iron powder treated with the sulfur-containing compound. The ratio of amounts of the usual untreated iron powder to the treated iron powder is 99/1 to 0/100 (by weight). When an amount of the treated iron powder is small, since the initial temperature elevation is slow and gas tends to be generated, it is preferable to previously add a gas generation inhibitor.

In the exothermic compositions of the present invention, there are employed 20 to 70 parts of water, 0.1 to 80 parts of the oxidation catalysts, 1 to 20 parts of the neutral metal salts, 1 to 500 parts of the water holding agents, and if necessary 0.1 to 4 parts of the gas generation inhibitors on the basis of 100 parts of the treated iron powders. The usual untreated iron powders may be used in the above-mentioned range. In addition, perfumes, moxa and heat accumulating agents may also be added.

These components can be mixed by usual mixing methods. All components may be mixed in one step, or a mixture of the mugwort leaf powder and the other water-holding agents is prepared, and then is mixed with the other components. The latter method is preferable. In this case, though the cotton-like or fibrous moxa is hardly mixed uniformly with the other components, the mugwort leaf powder from which the vein is removed can easily be mixed.

The thus prepared exothermic compositions of the present invention have uniformly distributed components and are dry and flowable.

The compositions of the invention are useful as exothermic compositions for body warmers. In this use, the compositions are packed into an air-permeable inner bag and an air-tight outer bag. According to this embodiment, there are advantages that the body warmer can fit a user's body and give a soft warmth. This is because the mugwort leaf powder has an excellent softness which is absent in the conventional water holding agents.

Materials of the outer bag are not limited insofar as they are air tight. Laminated films may be employed. Preferred examples of the outer bag are, for instance, films made of OPP, CPP; films of nyrons, polyesters and polypropyrenes having a moisture barrier coating of polyvinylidene chloride thereon; aluminum foil; plastic films having an aluminum deposition layer; and the like. The inner bag may be made by usual air-permeable materials such as nonwoven fabrics, woven fabrics and papers.

The present invention is more specifically described and explained by means of the following Examples. It is to be understood that the present invention is not limited to the Examples, and various changes and modifications may be made in the invention without departing from the spirit and scope thereof.

PREPARATION EXAMPLES 1 TO 4

An ammonium sulfate powder (particle size: 100 meshes pass) was added in the amount shown in Table 1 to 200 g of a reduced iron powder (particle size: 60 meshes pass), and mixed well so as to disperse the ammonium sulfate powder uniformly. The obtained mixture was placed in a glass vessel, heated at the temperature shown in Table 1, and kept at that temperature for 30 minutes to give an iron powder treated with ammonium sulfate.

EXAMPLE 1 TO 4

An exothermic composition was prepared by mixing 25 g of the treated iron powder obtained in each of Preparation Examples 1 to 4, with 10.5 g of water, 1.5 g of sodium chloride and 10.5 g of a wood powder.

A degree of initial heat generation of the composition (evaluated by the time required from 8° C. to 30° C. or 40° C.) was measured by packing the composition in an air-permeable bag. The bag was made of a polyethylene-laminated nylon nonwoven fabric and had 315 through holes (0.3 mm in diameter) at one side which were arranged in the center at 4.3 mm width and at a distance of 6 mm.

The measurement was carried out in a room maintained at a temperature of 8° C. by shaking the bag several tens of times, putting the bag and a thermo-couple on four blankets, and then covering them with two blankets.

The results are shown in Table 1.

COMPARATIVE EXAMPLE 1

The same procedures as in Example 1 were repeated except that a reduced iron powder was employed to prepare an expothermic composition instead of the iron powder treated with ammonium sulfate. The composition was packed in the same bag as used in Example 1 and the degree of initial heat generation of the composition was measured in the same manner as in Example 1.

The results are shown in Table 1.

COMPARATIVE EXAMPLES 2 TO 3

The same procedures as in Example 1 were repeated except that a ferrous sulfide powder (first class reagent available from Wako Junyaku Kogyo Kabushiki Kaisha) or an iron pyrite powder was employed instead of the iron powder treated with ammonium sulfate to prepare an exothermic composition. The composition was packed in the same bag as used in Example 1 and the degree of initial heat generation of the composition was measured in the same manner as in Example 1.

The results are shown in Table 1.

TABLE 1

| No. | Amount of ammonium sulfate (g) | Treating temperature (°C.) | Time (min) To 30° C. | Time (min) To 40° C. |
|---|---|---|---|---|
| Example | | | | |
| 1 | 0.8 | 300 | 36 | 88 |
| 2 | 0.8 | 200 | 37 | 80 |
| 3 | 0.08 | 200 | 38 | 93 |
| 4 | 0.01 | 200 | 55 | 99 |
| Com. Ex. | | | | |
| 1 | — | — | 85 | 160 |
| 2 | FeS | — | not reached | not reached |
| 3 | FeS$_2$ | — | not reached | not reached |

COMPARATIVE EXAMPLES 4

The same precedures as in Example 1 were repeated except that an untreated iron powder and ferrous sulfate were employed instead of the iron powder treated with ammonium sulfate and sodium chloride respectively to prepare an exothermic composition. The composition was packed in the same bag as used in Example 1 and the degree of initial heat generation of the composition was measured in the same manner as in Example 1.

It took 105 minutes for the temperature to rise to 30° C. and took 200 minutes to rise to 40° C. The comparative exothermic composition required longer time than in Comparative Example 1 where the untreated iron powder was used.

PREPARATION EXAMPLES 5 TO 9

An ammonium thiosulfate powder (particle size: 20 meshes pass, sodium thiosulfate content: about 30% by weight) was added in the amount shown in Table 2 to 200 g of a reduced iron powder (particle size: 60 meshes pass), and mixed well so as to disperse the ammonium thiosulfate powder uniformly. The obtained mixture was placed in a glass vessel, heated to the temperature shown in Table 2 for 30 minutes, and kept at that temperature for 30 minutes to give an iron powder treated with ammonium thiosulfate.

EXAMPLES 5 TO 9

An exothermic composition was prepared by mixing 25 g of the treated iron powder obtained in each Preparation Example 5 to 9, 10.5 g of water, 1.5 g of sodium chloride and 10.5 g of a wood powder. The composition was packed in the same bag as used in Example 1 and the degree of initial heat generation was measured in the same manner as in Example 1.

The results are shown in Table 2.

TABLE 2

| Example No. | Amount of ammonium thiosulfate (g) | Treating temperature (°C.) | Time (min) To 30° C. | Time (min) To 40° C. |
|---|---|---|---|---|
| 5 | 0.9 | 200 | 31 | 70 |
| 6 | 0.45 | 200 | 39 | 79 |
| 7 | 0.45 | 100 | 38 | 73 |
| 8 | 0.1 | 200 | 36 | 78 |
| 9 | 0.01 | 200 | 40 | 80 |

PREPARATION EXAMPLES 10 TO 13

An ammonium sulfamate powder (particle size: 20 meshes pass) was added in the amount shown in Table 3 to 200 g of a reduced iron powder (particle size: 60 meshes pass), and mixed well so as to disperse the ammonium sulfamate powder uniformly. The obtained mixture was placed in a glass vessel, heated to the temperature shown in Table 3 for 30 minutes, and kept at that temperature for 30 minutes to give an iron powder treated with ammonium sulfamate.

EXAMPLES 10 TO 13

An exothermic composition was prepared by mixing 25 g of the treated iron powder obtained in each Preparation Example 10 to 13, 10.5 g of water, 1.5 g of sodium chloride and 10.5 g of a wood powder. The composition was packed in the same bag as used in Example 1 and the degree of initial heat generation was measured in the same manner as in Example 1.

The results are shown in Table 3.

TABLE 3

| Example No. | Amount of ammonium sulfamate (g) | Treating temperature (°C.) | Time (min) To 30° C. | Time (min) To 40° C. |
|---|---|---|---|---|
| 10 | 0.7 | 300 | 39 | 100 |
| 11 | 0.7 | 200 | 45 | 99 |
| 12 | 0.7 | 100 | 61 | 103 |
| 13 | 0.07 | 200 | 44 | 101 |

PREPARATION EXAMPLE 14

0.5 Gram of an aqueous ammonium sulfide solution (available from Wako Junyaku Kogyo Kabushiki Kaisha) was added to 200 g of a reduced iron powder (particle size: 60 meshes pass), and mixed well so as to wet the iron powder with the solution uniformly. The obtained mixture was placed in a glass vessel, heated to 200° C. for 30 minutes, and kept at that temperature for 30 minutes to give an iron powder treated with ammonium sulfide.

EXAMPLE 14

An exothermic composition was prepared by mixing 25 g of the treated iron powder obtained in Preparation Example 14, 10.5 g of water, 1.5 g of sodium chloride and 10.5 g of a wood powder. The composition was packed in the same bag as used in Example 1 and the degree of initial heat generation was measured in the same manner as in Example 1.

The time required for a temperature rise from 8° to 30° C. was 45 minutes and the time for a from 8° to 40° C. was 95 minutes.

PREPARATION EXAMPLES 15 TO 17.

0.6 Gram of liquid thioglycollic acid (super class reagent available from Wako Junyaku Kogyo Kabushiki Kaisha) was added to 200 g of a reduced iron powder (particle size: 60 meshes pass), and mixed well so as to wet the iron powder with the liquid uniformly. The obtained mixture was placed in a glass vessel, heated to the temperature shown in Table 4 for 30 minutes, and kept at that temperature for 30 minutes to give an iron powder treated with thioglycollic acid.

EXAMPLES 15 TO 17

An exothermic composition was prepared by mixing 25 g of the treated iron powder obtained in each Preparation Example 15 to 17, 10.5 g of water, 1.5 g of sodium chloride and 10.5 g of a wood powder. The composition was packed in the same bag as used in Example 1 and the degree of initial heat generation was measured in the same manner as in Example 1.

The results are shown in Table 4.

TABLE 4

| Example No. | Amount of thioglycollic acid (g) | Treating temperature (°C.) | Time (min) To 30° C. | To 40° C. |
|---|---|---|---|---|
| 15 | 0.6 | 300 | 22 | 42 |
| 16 | 0.6 | 200 | 24 | 45 |
| 17 | 0.6 | 120 | 37 | 80 |

PREPARATION EXAMPLES 18 TO 20

0.4 Gram of a thiourea powder (particle size: 20 meshes pass) was added to 200 g of a reduced iron powder (particle size: 60 meshes pass), and mixed well so as to disperse the thiourea powder uniformly. The obtained mixture was placed in a glass vessel, heated to the temperature shown in Table 5 for 30 minutes, and kept at that temperature for 30 minutes to give an iron powder treated with thiourea.

EXAMPLES 18 TO 20

An exothermic composition was prepared by mixing 25 g of the treated iron powder obtained in each Preparation Example 18 to 20, 10.5 g of water, 1.5 g of sodium chloride and 10.5 g of a wood powder. The composition was packed in the same bag as used in Example 1 and the degree of initial heat generation was measured in the same manner as in Example 1.

The results are shown in Table 5.

TABLE 5

| Example No. | Amount of thiourea (g) | Treating temperature (°C.) | Time (min) To 30° C. | To 40° C. |
|---|---|---|---|---|
| 18 | 0.4 | 300 | 30 | 67 |
| 19 | 0.4 | 200 | 43 | 90 |
| 20 | 0.4 | 100 | 50 | 106 |

PREPARATION EXAMPLES 21 TO 23

0.7 Gram of a sodium diethyldithiocarbamate powder (particle size: 20 meshes pass) was added to 200 g of a reduced iron powder (particle size: 60 meshes pass), and mixed well so as to disperse the sodium diethyldithiocarbamate powder uniformly. The obtained mixture was placed in a glass vessel, heated to the temperature shown in Table 6 for 30 minutes, and kept at that temperature for 30 minutes to give an iron powder treated with sodium diethyldithiocarbamate

EXAMPLES 21 TO 23

An exothermic composition was prepared by mixing 25 g of the treated iron powder obtained in each Preparation Example 21 to 23, 10.5 g of water, 1.5 g of sodium chloride and 10.5 g of a wood powder. The composition was packed in the same bag as used in Example 1 and a degree of initial heat generation was measured in the same manner as in Example 1.

The results are shown in Table 6.

TABLE 6

| Example No. | Amount of sodium diethyldithiocarbamate (g) | Treating temperature (°C.) | Time (min) To 30° C. | To 40° C. |
|---|---|---|---|---|
| 21 | 0.7 | 300 | 43 | 88 |
| 22 | 0.7 | 200 | 41 | 84 |
| 23 | 0.7 | 100 | 56 | 112 |

PREPARATION EXAMPLE 24

0.9 Gram of a sodium sulfate powder (particle size: 20 meshes pass) was added to 200 g of a reduced iron powder (particle size: 60 meshes pass), and mixed well so as to disperse the sodium sulfate powder uniformly. The obtained mixture was placed in a glass vessel, heated to 200° C. for 30 minutes, and kept at that temperature for 30 minutes to give an iron powder treated with sodium sulfate.

EXAMPLE 24

An exothermic composition was prepared by mixing 25 g of the treated iron powder obtained in Preparation Example 24, 10.5 g of water, 1.5 g of sodium chloride and 10.5 g of a wood powder. The composition was packed in the same bag as used in Example 1 and the degree of initial heat generation was measured in the same manner as in Example 1.

The time required for a temperature rise from 8° to 30° C. was 57 minutes and the time required for a temperature rise from 8° to 40° C. was 105 minutes.

PREPARATION EXAMPLE 25

A mixture of 0.9 g of a sodium sulfate powder and 0.7 g of an ammonium chloride powder was added to 200 g of a reduced iron powder (particle size: 60 meshes pass), and mixed well so as to disperse the sulfur-containing compound powders uniformly. The obtained mixture was placed in a glass vessel, heated to 200° C. for 30 minutes, and kept at that temperature for 30 minutes to give an iron powder treated with the sulfur-containing compounds.

EXAMPLE 25

An exothermic composition was prepared by mixing 25 g of the treated iron powder obtained in Preparation Example 25, 10.5 g of water, 1.5 g of sodium chloride and 10.5 g of a wood powder. The composition was packed in the same bag as used in Example 1 and the degree of initial heat generation was measured in the same manner as in Example 1.

The time required for a temperature rise from 8° to 30° C. was 20 minutes and the time required for a temperature rise from 8° to 40° C. was 44 minutes.

PREPARATION EXAMPLE 26

A mixture of 0.7 g of a sodium thiosulfate powder and 0.3 g of an ammonium chloride powder was added to 200 g of a reduced iron powder (particle size: 60 meshes pass), and mixed well so as to disperse the sulfur-containing compound powders uniformly. The obtained mixture was placed in a glass vessel, heated to 0° C. for 30 minutes, and kept at that temperature for 30 minutes to give an iron powder treated with the sulfur-containing compounds.

EXAMPLE 26

An exothermic composition was prepared by mixing 25 g of the treated iron powder obtained in Preparation Example 26, 10.5 g of water, 1.5 g of sodium chloride and 10.5 g of a wood powder. The composition was packed in the same bag as used in Example 1 and the degree of initial heat generation was measured in the same manner as in Example 1.

The time required for a temperature rise from 8° to 30° C. was 27 minutes and time for a temperature rise from 8° to 40° C. was 54 minutes.

PREPARATION EXAMPLE 27

A mixture of 0.5 g of a sodium sulfide powder and 0.7 g of an ammonium chloride powder was added to 200 g of a reduced iron powder (particle size: 60 meshes pass), and mixed well so as to disperse the sulfur-containing compound powders uniformly. The obtained mixture was placed in a glass vessel, heated and kept at the temperature for 30 minutes to give an iron powder treated with the sulfur-containing compounds.

EXAMPLE 27

An exothermic composition was prepared by mixing 25 g of the treated iron powder obtained in Preparation Example 27, 10.5 g of water, 1.5 g of sodium chloride and 10.5 g of a wood powder. The composition was packed in the same bag as used in Example 1 and the degree of initial heat generation was measured in the same manner as in Example 1.

The time required for a temperature rise from 8° to 30° C. was 55 minutes and the time required for a temperature rise from 8° to 40° C. was 115 minutes.

PREPARATION EXAMPLE 28

0.3 Gram of a simple sulfur powder (particle size: 100 meshes pass) was added to 200 g of a reduced iron powder (particle size: 60 meshes pass), and mixed well so as to disperse the simple sulfur powder uniformly. The obtained mixture was placed in a glass vessel, heated to 200° C. for 30 minutes, and kept at that temperature for 30 minutes to give an iron powder treated with the simple sulfur.

EXAMPLE 28

An exothermic composition was prepared by mixing 25 g of the treated iron powder obtained in Preparation Example 28, 10.5 g of water, 1.5 g of sodium chloride and 10.5 g of a wood powder. The composition was packed in the same bag as used in Example 1 and the degree of initial heat generation was measured in the same manner as in Example 1.

The time required for a temperature rise from 8° to 30° C. was 37 minutes and the time for a temperature rise from 8° to 40° C. was 77 minutes.

EXAMPLES 29 TO 40

An exothermic composition was prepared by mixing 25 g of the treated iron powder shown in Table 7, 12.5 g of water, 1.7 g of sodium chloride, 3 g of vermiculite, 2.5 g of an active carbon (E-30 available from Takeda Chemical Industries, Ltd.), 1.1 g of the mugwort leaf powder and 0.83 g of a water absorbing resin (SAN-WET IM-300 available from SANYO CHEMICAL INDUSTRIES, LTD.). The composition was packed in the same bag as used in Example 1, and a heat generation history thereof was measured in the same manner as in Example 1.

The results are shown in Table 7.

TABLE 7

| Ex. No. | Treated iron powder | Temperature (°C.) Equilibrium | Temperature (°C.) Maximum | Time (minutes) To 40° C. | Time (minutes) To equi. temp. | Retention time (hours) Above equi. temp. | Retention time (hours) Above 40° |
|---|---|---|---|---|---|---|---|
| 29 | Prep. Ex. 2 | 55 | 58 | 25 | 116 | 8.5 | 16.5 |
| 30 | Prep. Ex. 6 | 55 | 59 | 23 | 110 | 8.2 | 13.8 |
| 31 | Prep. Ex. 11 | 55 | 60 | 25 | 118 | 8.0 | 16.3 |
| 32 | Prep. Ex. 14 | 55 | 58 | 25 | 130 | 7.8 | 17.0 |
| 33 | Prep. Ex. 16 | 57 | 62 | 18 | 96 | 7.0 | 13.2 |
| 34 | Prep. Ex. 19 | 55 | 58 | 24 | 126 | 9.0 | 18.0 |
| 35 | Prep. Ex. 22 | 57 | 63 | 24 | 114 | 8.0 | 16.3 |
| 36 | Prep. Ex. 24 | 55 | 60 | 23 | 112 | 7.7 | 14.0 |
| 37 | Prep. Ex. 25 | 55 | 60 | 21 | 102 | 7.5 | 13.7 |
| 38 | Prep. Ex. 26 | 55 | 59 | 25 | 124 | 8.0 | 16.0 |
| 39 | Prep. Ex. 27 | 55 | 56 | 26 | 135 | 8.3 | 16.3 |
| 40 | Prep. Ex. 28 | 55 | 59 | 22 | 110 | 8.1 | 16.2 |

EXAMPLES 41 TO 44 AND COMPARATIVE EXAMPLES 5 TO 6

An exothermic composition was prepared by uniformly mixing 25 g of the treated iron powder shown in Table 8, 12 g of water, 1.5 g of sodium chloride, 2.5 g of vermiculite, 2.5 g of an active carbon (E-30), 1.1 g of the mugwort leaf powder, 4.4 g of coconut husk charcoal and 0.83 g of a water absorbing resin powder (SAN-WET IM-300). The exothermic composition was packed in an air-tight aluminium foil bag under vacuum, and sealed.

The sealed bag was heated at 88° C. for 8 hours in a dryer, and the degree of gas generation was measured by observing the appearance of the bag with the naked eye.

⊚: No change
○: Almost no change
×: Expanded and some being exploded

For comparison, the same measurement was carried out with respect to a composition containing an untreated reduced iron powder instead of the treated iron powder (Comparative Example 5) and a composition containing an untreated reduced iron powder and ferrous sulfate instead of the treated iron powder and sodium chloride respectively (Comparative Example 6).

The results are shown in Table 8.

TABLE 8

| Ex. No. | Iron Powder | Gas generation |
|---|---|---|
| 41 | Prep. Ex. 5 | ○ |
| 42 | Prep. Ex. 16 | ⊚ |
| 43 | Prep. Ex. 19 | ○ |
| 44 | Prep. Ex. 22 | ⊚ |
| Comp. Ex. 5 | Untreated reduced iron powder | × |
| Comp. Ex. 6 | Untreated reduced iron powder + Ferrous sulfate | × |

EXAMPLES 45 TO 46 AND COMPARATIVE EXAMPLES 7 TO 8

A water holding agent shown in Table 9 was placed in a beaker in an amount shown in Table 9, and water was pored onto the water holding agent. After mixing well for 2 minutes, the beaker was tilted. The water holding capacity was defined by the largest amount of water that could be pored onto the water holding agent without water flowing out when the beaker was tilted.

The water holding capacities of the water holding agents are shown in Table 9.

TABLE 9

| | Water holding agent (g) | Water holding capacity (g) |
|---|---|---|
| Ex. No. | | |
| 45 | Mugwort leaf powder (10) | 26.5 |
| 46 | Mugwort leaf powder (5) + coconut husk charcoal (5) | 17.0 |
| Comp. Ex. 7 | Active carbon (10) | 17.0 |
| Comp. Ex. 6 | Coconut husk charcoal (10) | 8.0 |

As is clear from Table 9, the water holding capacity of the mugwort leaf powder is 1.5 to 4 times larger than that of the active carbon and the coconut husk charcoal. This result shows that the mugwort leaf powder is a very effective water holding agent.

According to the exothermic compositions of the present invention, the initial heat generation can be accelerated and the gas generation can be inhibited. Further, since mugwort leaf powder which is lighter, cheaper and higher in water holding capacity than conventional water holding agents is employed, the composition can be reduced in both volume and weight. Moreover since mugwort leaf powder can be dispersed uniformly into the other components and has a good powder flowability, the package operation can be improved, which can save manufacturing cost.

What we claim is:

1. In exothermic compositions comprising iron powders, neutral metal salts, water, and water holding agents, the improvement which comprises that iron powders treated with sulfur-containing compounds are employed as the iron powders and that dry powders of mugwort leaves from which veins are removed are employed as a part of the water holding agents.

2. The compositions of claim 1, wherein the sulfur-containing compounds are organic sulfur-containing compounds.

3. The compositions of claim 1, wherein the sulfur-containing compounds are inorganic sulfur-containing compounds.

4. The compositions of claim 1, wherein the sulfur-containing compounds are simple sulfur.

5. The compositions of claim 1, wherein the sulfur-containing compounds are sulfur- and nitrogen-containing compounds.

6. The compositions of claim 1, wherein the water holding agents are mixtures of the mugwort leaf dry powders and at least one member selected from the group consisting of wood powder, coconut husk charcoal powder, silica gel powder, vermiculite powder, pearlite powder, polyurethane foam powder, asbestos powder and water absorbing resin powder.

7. The composition of claim 1, which further comprises oxidation catalysts.

8. The compositions of claim 7, wherein the composition comprises:
   100 parts by weight of the iron powders treated with the sulfur-containing compounds,
   1 to 20 parts by weight of the neutral metal salts,
   0.1 to 80 parts by weight of the oxidation catalysts,
   1 to 500 parts by weight of the water holding agents which contains 5 to 55% by weight of the mugwort leaf dry powder, and
   20 to 70 parts by weight of water.

* * * * *

UNITED STATES PATENT AND TRADEMARK OFFICE
CERTIFICATE OF CORRECTION

PATENT NO. : 4,649,895

DATED : March 17, 1987

INVENTOR(S) : Ryuichi YASUKI et al

It is certified that error appears in the above-identified patent and that said Letters Patent is hereby corrected as shown below:

On the cover page, Item [73], after "Co.," insert --Ltd.--.

Column 1, line 66, "housing" should read --having--.

Column 2, line 18, "sufuric" should read --sulfuric-- and "thiosufuric" should read --thiosulfuric--.

Signed and Sealed this

Second Day of February, 1988

Attest:

DONALD J. QUIGG

Attesting Officer

Commissioner of Patents and Trademarks